United States Patent
Usey

(10) Patent No.: US 9,594,480 B1
(45) Date of Patent: *Mar. 14, 2017

(54) SYSTEM, METHOD, AND COMPUTER-READABLE MEDIUM FOR FACILITATING ADAPTIVE TECHNOLOGIES

(71) Applicant: OPEN INVENTION NETWORK LLC, Durham, NC (US)

(72) Inventor: Matthew Kevin Usey, Allen, TX (US)

(73) Assignee: Open Invention Network LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/090,308

(22) Filed: Apr. 4, 2016

Related U.S. Application Data

(63) Continuation of application No. 12/499,463, filed on Jul. 8, 2009, now Pat. No. 9,304,601.

(51) Int. Cl.
| | |
|---|---|
| *G09B 21/00* | (2006.01) |
| *G06F 3/0484* | (2013.01) |
| *G06F 3/0487* | (2013.01) |
| *G06F 3/0481* | (2013.01) |
| *H04N 1/00* | (2006.01) |
| *H04N 13/04* | (2006.01) |

(52) U.S. Cl.
CPC .......... *G06F 3/0484* (2013.01); *G06F 3/0481* (2013.01); *G06F 3/0487* (2013.01); *H04N 1/00514* (2013.01); *H04N 13/0468* (2013.01)

(58) Field of Classification Search
CPC .... G09B 19/00; G09B 21/00; H04N 1/00514; H04N 13/0468

USPC ......... 434/112, 236, 322, 323, 350; 715/865
See application file for complete search history.

(56) References Cited

U.S. PATENT DOCUMENTS

| | | | | |
|---|---|---|---|---|
| 3,781,802 A * | 12/1973 | Kafafian | ................ | G09B 21/00 340/4.12 |
| 5,931,791 A * | 8/1999 | Saltzstein | ............ | A61B 5/0205 128/904 |
| 6,554,618 B1 * | 4/2003 | Lockwood | ............... | G09B 7/00 434/118 |
| 2002/0086272 A1 * | 7/2002 | Ho | .......................... | G09B 5/06 434/236 |
| 2003/0129574 A1 * | 7/2003 | Ferriol | ..................... | G09B 5/00 434/362 |
| 2007/0063998 A1 * | 3/2007 | Mahesh | ................ | G06F 19/321 345/419 |
| 2007/0141541 A1 * | 6/2007 | Chan | ........................ | G09B 5/06 434/236 |
| 2008/0228868 A1 * | 9/2008 | Sivakoff | .................. | G09B 7/02 709/203 |

(Continued)

*Primary Examiner* — Andrew Iwamaye
*Assistant Examiner* — Jerry-Daryl Fletcher
(74) *Attorney, Agent, or Firm* — Haynes and Boone, LLP

(57) ABSTRACT

A system, method, and computer-readable medium that facilitate software configuration of assistive computer devices by automatically assessing a user's capabilities through questions and tasks are provided. The analysis results of the user's capabilities are then available to assistive computer software applications which may subsequently update their interfaces accordingly. A mapping mechanism from an external input device into a target software application is facilitated for software applications that do not include assistive technology features.

17 Claims, 7 Drawing Sheets

(56) References Cited

U.S. PATENT DOCUMENTS

2009/0089718 A1\* 4/2009 Pompilio ............ G06F 9/4446
715/865

\* cited by examiner

SYSTEM, METHOD, AND COMPUTER-READABLE MEDIUM FOR FACILITATING ADAPTIVE TECHNOLOGIES

CROSS REFERENCE TO RELATED APPLICATIONS

This application is a continuation of U.S. application Ser. No. 12/499,463, filed Jul. 8, 2009, entitled "SYSTEM, METHOD, AND COMPUTER-READABLE MEDIUM FOR FACILITATING ADAPTIVE TECHNOLOGIES", issued U.S. Pat. No. 9,304,601, issued Apr. 4, 2016, the entire contents are incorporated herein by reference.

FIELD OF THE INVENTION

The present invention is generally related to data processing systems and, more particularly, to mechanisms that facilitate adaptation of user input devices according to a user skill.

BACKGROUND OF THE INVENTION

Computer systems and other interactive electronic products, e.g., mobile phones, personal digital assistants (PDAs), music players, etc., currently offer multiple methods for a user to provide input. In addition, assistive technology products are designed to provide additional accessibility to individuals who have physical or cognitive difficulties, impairments, and disabilities. These assistive products allow disabled users to access other products in a manner customized to their condition. They may take the form of custom hardware deployed between the user and the product of interest, herein referred to as the target product. The hardware may act as an interface between the user and the target product, translating the inputs and outputs of both the user and the target product in order to facilitate interaction between the user and the target product.

In addition to hardware, assistive technologies may take the form of software. In this case, the assistive software may run alongside a software target, providing the interface as in the hardware case.

In many cases involving a hardware assistive product that is connected to a computer or other electronic device, the assistive technology suite may also contain a software component. In all cases, the purpose of the assistive technology product is to provide a disabled user an operable interface to a previously inaccessible product or a product of limited accessibility.

Concerning an individual interacting with a computer or other electronic device, alternative input devices allow control of the device through means other than a standard keyboard or pointing device.

Examples of assistive technologies include:

Alternative keyboards featuring larger, or smaller, than standard keys or keyboards, alternative key configurations, and keyboards for use with one hand;

Electronic pointing devices that are used to control the cursor on the screen without the use of hands. Devices used may include ultrasound, infrared beams, eye movements, nerve signals, or brain waves;

Sip-and-puff systems that are activated by inhaling or exhaling;

Wands and sticks that may be worn on the head, held in the mouth or strapped to the chin and used to press keys on the keyboard;

Joysticks that may be manipulated by hand, feet, chin, etc., and that are used to control a cursor on a screen;

Trackballs featuring movable balls on top of a base that may be used to move a cursor on a screen;

Touch screens that allow direct selection or activation of the device by touching the screen thereby making it easier to select an option directly rather than through a mouse movement or keyboard. Touch screens are either built into the computer monitor or may be added onto a computer monitor;

Braille embossers that transfer computer generated text into embossed Braille output. Braille translation programs convert text scanned-in or generated via standard word processing programs into Braille, which can be printed on the embosser;

Keyboard filters that provide typing aids, such as word prediction utilities and add-on spelling checkers, that reduce the required number of keystrokes. Keyboard filters enable users to quickly access the letters they need and to avoid inadvertently selecting keys they don't intend to select;

Light signalers that alert monitor computer sounds and alert the computer user with light signals. Such mechanisms may be useful when a computer user can not hear computer sounds or is not directly in front of the computer screen. As an example, a light may flash thereby alerting the user when a new e-mail message has arrived or a computer command has completed;

On-screen keyboards that provide an image of a standard or modified keyboard on the computer screen that allows the user to select keys with a mouse, touch screen, trackball, joystick, switch, or electronic pointing device. On-screen keyboards often have a scanning option that highlights individual keys that may be selected by the user. On-screen keyboards are helpful for individuals who are not able to use a standard keyboard due to dexterity or mobility difficulties;

Reading tools and learning disabilities programs that include software and hardware designed to make text-based materials more accessible for people who have difficulty with reading. Options may include scanning, reformatting, navigating, or speaking text out loud. These programs are helpful for those who have difficulty seeing or manipulating conventional print materials, people who are developing new literacy skills or who are learning English as a foreign language, and people who comprehend better when they hear and see text highlighted simultaneously;

Refreshable Braille displays that provide tactile output of information represented on the device screen. A Braille "cell" is composed of a series of dots. The pattern of the dots and various combinations of the cells are used in place of letters. Refreshable Braille displays mechanically lift small rounded plastic or metal pins as needed to form Braille characters. The user reads the Braille letters with his or her fingers, and then, after a line is read, can refresh the display to read the next line;

Screen enlargers, or screen magnifiers, that work like a magnifying glass for the device by enlarging a portion of the screen which can increase legibility and make it easier to see items on the computer. Some screen enlargers allow a person to zoom in and out on a particular area of the screen;

Screen readers that are used to verbalize, or "speak," everything on the screen including text, graphics, control buttons, and menus into a computerized voice that is spoken aloud. In essence, a screen reader transforms a graphic user interface (GUI) into an audio interface. Screen readers are essential for computer users who are blind;

Speech recognition or voice recognition programs that allow people to give commands and enter data using their voices rather than a mouse or keyboard. Voice recognition systems use a microphone attached to the computer, which can be used to create text documents, such as letters or e-mail messages, browse the Internet, and navigate among applications and menus by voice;

Text-to-Speech (TTS), or speech synthesizers, that receive information be conveyed to the screen in the form of letters, numbers, and punctuation marks, and then "speak" it out loud in a computerized voice. Using speech synthesizers allows computer users who are blind or who have learning difficulties to hear what they are typing and also provide a spoken voice for individuals who can not communicate orally, but can communicate their thoughts through typing;

Talking and large-print word processors comprising software programs that use speech synthesizers to provide auditory feedback of what is typed. Large-print word processors allow the user to view everything in large text without added screen enlargement; and TTY/TDD conversion modems that are connected between electronic devices and telephones to allow an individual to type a message on an electronic device and send it to a TTY/TDD telephone or other Baudot equipped device;

Many companies have declared a commitment to accessibility. For example, accessibility features are built into many of Microsoft's products, from operating systems such as Windows Vista, that include an Ease of Access Center to software applications, and Microsoft Word that includes zoom and auto-correct features. The Apple Macintosh OSX platform is compatible with many assistive technology products.

An example assistive technology for mobile phones is deployed on the Google Android G1 phone that features a magnification mechanism that is beneficial to individuals with vision impairments. Once activated, '+' and '−' signs appear on the bottom of the screen allowing the user to enlarge or reduce the page. In addition, a double click of the scroll wheel allows the user to move a "magnification square" that magnifies the portion beneath it.

The Linux operating system may be run through a non-graphical, text-only environment or through a graphical user interface. The non-graphical interface is useful for visually impaired individuals because, with the help of a screen reader and speech synthesizer, they can have access to the full functionality of the system. Also, for the graphical interface, different windowing systems, such as KDE or GNOME, have accessibility projects.

Despite the obvious benefits given by the current assistive technology products, the goal of many disabled individuals is independence, and these products may require significant assistance from able-bodied individuals in order for proper configuration for a given disabled individual. In addition, an individual's disability is frequently varied from day to day. Thus, a given configuration may be appropriate one day but less than optimal the next day. This variability may be caused by natural day-to-day fluctuations in the individual's condition, caused by a gradual reduction in a user's abilities due to a degenerative condition, or caused by a gradual improvement in a user's abilities due, for example, to increased muscle tone thanks to daily practice using the assistive devices. In these variable cases, the disabled individual might not have the capability to reconfigure the assistive technology device without assistance.

Therefore, what is needed is a mechanism that overcomes the described problems and limitations.

SUMMARY OF THE INVENTION

The present invention provides a system, method, and computer-readable medium that facilitate software configuration of assistive computer devices by automatically assessing a user's capabilities through questions and tasks. The analysis results of the user's capabilities are then available to assistive computer software applications which may subsequently update their interfaces accordingly. A mapping mechanism from an external input device into a target software application is facilitated for software applications that do not include assistive technology features.

In one embodiment, a method of adapting data processing system operational characteristics to a user is provided. The method includes receiving, by the data processing system, a discrete user input from an input device, assessing whether the user is able to utilize one or more other input devices, for each input device able to be utilized by the user, performing a proficiency test for the respective input device, and modifying an operational characteristic of the data processing system based on results of the proficiency test.

In another embodiment, a computer-readable medium having computer-executable instructions for execution by a processing system, the computer-executable instructions for adapting data processing system operational characteristics to a user is provided. The computer-readable medium comprises instructions that, when executed, cause the processing system to receive, by the data processing system, a discrete user input from an input device, assess whether the user is able to utilize one or more other input devices, for each input device able to be utilized by the user, perform a proficiency test for the respective input device, wherein the proficiency test evaluates a quality of user input supplied to the respective input device, and modify an operational characteristic of the data processing system based on results of the proficiency test.

In another embodiment, a data processing system for modifying operational characteristics for a user is provided. The data processing system includes a processing module, a memory device including an adaptive software module, and an input device. The processing module receives a discrete user input from the input device, assesses whether the user is able to utilize one or more other input devices, for each input device able to be utilized by the user, performs a proficiency test for the respective input device, wherein the proficiency test evaluates a quality of user input supplied to the respective input device, and modifies an operational characteristic of the data processing system based on results of the proficiency test.

BRIEF DESCRIPTION OF THE DRAWINGS

Aspects of the present disclosure are best understood from the following detailed description when read with the accompanying figures, in which.

DETAILED DESCRIPTION OF THE INVENTION

Figure 1:
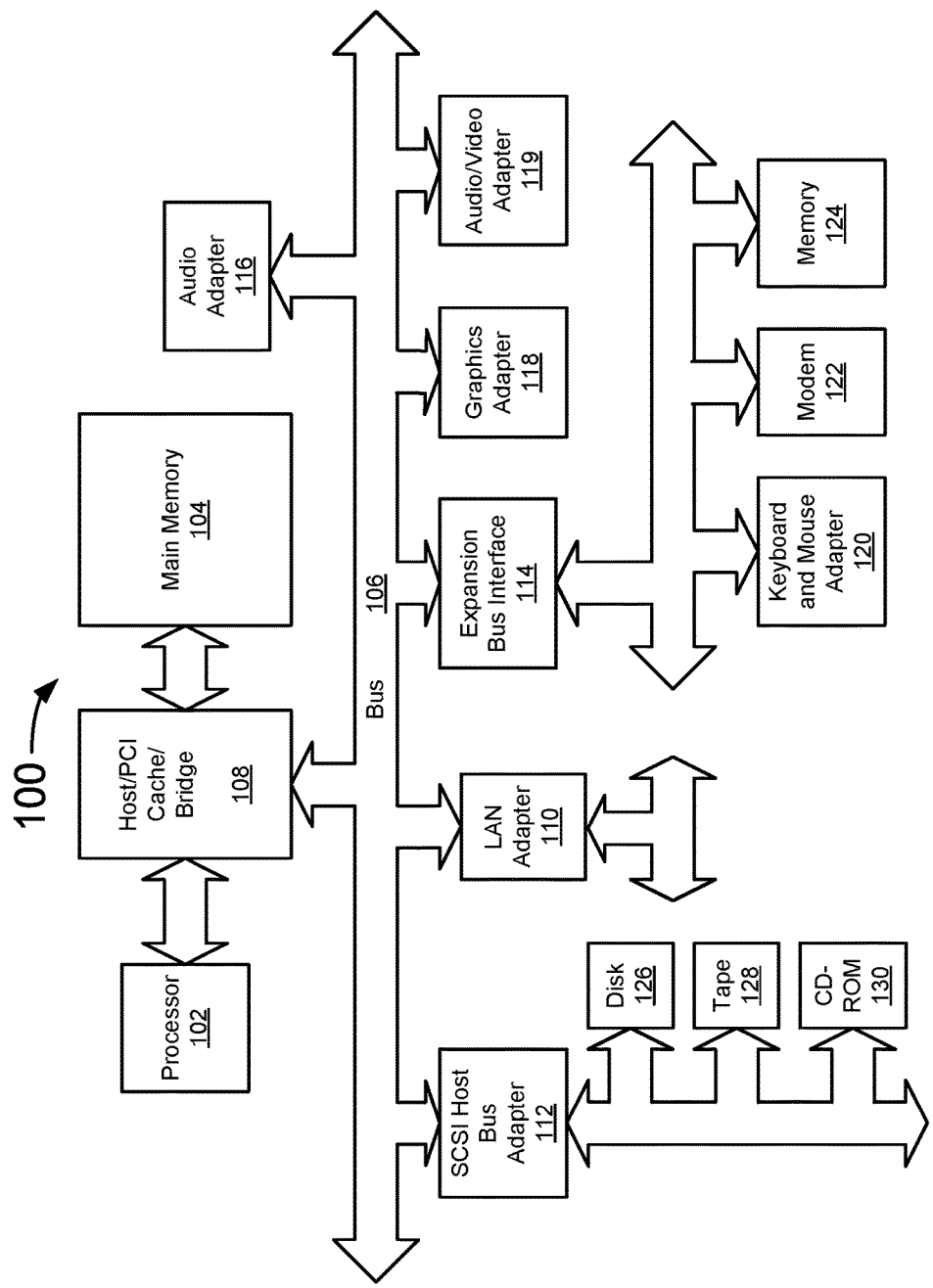
FIG. 1 depicts a diagrammatic representation of a data processing system in which embodiments of the present disclosure may be implemented.

It is to be understood that the following disclosure provides many different embodiments or examples for implementing different features of various embodiments. Specific examples of components and arrangements are described below to simplify the present disclosure. These are, of course, merely examples and are not intended to be limiting.

In accordance with disclosed embodiments, adaptive assistive technology mechanisms are provided that facilitate adaption of a product to a given user's abilities and to available hardware assistive devices. Disclosed mechanisms provides for system assessment of a user's capabilities and automated adjustment of a device.

Beyond devices designed specifically for the assistive technology market, there is also contemporary development of more sophisticated hardware pointer devices, such as a mouse or track pad, for able-bodied mainstream computer users. These efforts may take many forms, including the aesthetic design to devices, ergonomic changes to devices, operational changes to devices that do not affect the user, operational changes to devices that do affect the user, new devices which interact with the user in a traditional manner analogous to known devices, and new devices which exploit new methods of interaction with users.

For purposes of explanation, consider a pointing device comprising a mouse. With regard to aesthetic design of devices, neither the user's experience with the device nor the device's functionality is modified. Rather, the device is changed in order for it to be more appealing, particularly in a visual sense. For example, a mouse designer might change the colors or materials or may include an LED in the mouse to provide a different appearance. With regard to ergonomic changes, designers change the basic shape of a pointing device in order to improve the user's ability to interact with the device in a comfortable, non-injurious manner. For example, a mouse's shape may be modified through the addition of a thumb rest in order to facilitate proper wrist orientation when using the mouse. With regard to operational changes to a device that do not affect the user, the basic internal operation of the device is changed. For example, a mouse designer may replace the track ball and positional sensors of a mouse with a light source and an optical sensor. In this case, the user's interaction is not significantly modified, though the internal operation of the mouse is different. With regard to operational changes that affect the user, the user's interaction with the device is affected. For example, a mouse designer may add a new button or mouse wheel to the mouse. Or, the designer may simply add an extra axis of operation to an existing mouse feature, such as adding the ability to tilt a mouse wheel to the sides thereby adding horizontal scrolling capabilities to the vertical scrolling capabilities already provided by the wheel itself. With regard to new devices which interact with the user in a traditional manner analogous to a known device, a designer may utilize a given method of user interaction with a computer and change the device. For example, a user typically controls an onscreen pointer by using his hand to move a mouse around on a flat plane. The inventor of the track pad pointing device essentially removed the mouse altogether and placed the electronics into the plane itself. Therefore, the user operation is essentially the same—the user moves the user's hand around a horizontal plane to control the pointer, but the device itself has changed. With regard to new devices which exploit new methods of interaction with the user, a designer seeks completely new mechanisms of interaction thereby changing the entire man-machine interface. For the current discussion, the end result is the same. However, the user simply wants to control a cursor's position on a computer screen. For these methods, alternate control sources for controlling onscreen pointers are explored, such as the position of the eyes, the activation levels of certain muscles, and the strength and structure of brain waves. Obviously, the hardware required is completely different in these cases, and the user will interact with the devices in a completely different manner. Most users who purchase a new computer or other electronic system do not desire to use equipment that they are not familiar with. A new pointing device, for example, may be met by the general public with significant resistance if it is not immediately usable. What is needed is a technique or product by which a new pointing device, or other input device, may be gradually introduced to the consumer without adversely affecting their productivity in a significant manner. This need parallels the need of those who require assistive devices—they also desire efficient control of their electronic devices as soon as possible.

In accordance with disclosed embodiment, the functionality of assistive devices is increased by providing an adaptive software system that may be customized to a given user based directly on an automatic assessment of that user's abilities. In this manner, a disabled user has greater autonomy in configuring and adjusting an assistive device thereby advantageously allowing the user greater independence.

In another embodiment, an interactive assessment of the abilities of a user is provided while using, for example, a pointing device, and adjustments to the system requirements are made based on that user's abilities. In this manner, a beginner with a new device is provided a system that is optimized for their lower proficiency. For example, the buttons in applications may be displayed larger, and time requirements for user input will be loosened. In the manner, the user can still use the system, though the interface will be modified. Once the system detects that the user's abilities have evolved to a higher level of competency, input requirements will be reduced. In this manner, a new device may be introduced to the consumer while minimizing the barriers to user acceptance.

While there are multiple assistive technology products on the market to assist individuals with disabilities, contemporary systems require manual configuration and don't adapt to a user's condition automatically. In addition, new pointing devices or mechanisms used to interact with computers or other electronic devices necessitate user retraining. In accordance with disclosed embodiments, a mechanism referred to herein as AutoAdapt alleviates contemporary device shortcomings by providing a software layer that is deployed on the computing device between a software application, e.g., Microsoft Office software, Qualilife's QualiHome software, a mobile phone application, etc., and a physical input device. In this manner, user interactions with the device pass through the AutoAdapt layer before continuing in a new form to the final application. This functionality may be incorporated into the operating system of the device itself. A device featuring the AutoAdapt mechanism may advantageously assess a user's capabilities and provide the analysis to other accessibility-aware applications. For those non-accessible applications, an AutoAdapt mechanism may provide the signal conversion necessary to interact with the target application.

FIG. 1 depicts a diagrammatic representation of a data processing system 100, such as a desktop computer, in which embodiments of the present disclosure may be implemented. In the illustrative example, data processing system 100 employs a peripheral component interconnect (PCI) local bus architecture although other bus architectures, such as Accelerated Graphics Port (AGP) and Industry Standard Architecture (ISA), may be suitably substituted therefor. Processor 102 and main memory 104 are connected to PCI local bus 106 through PCI bridge 108. PCI bridge 108 also may include an integrated memory controller and cache memory for processor 102. Additional connections to PCI local bus 106 may be made through direct component interconnection or through add-in boards. In the depicted example, local area network (LAN) adapter 110, SCSI host bus adapter 112, and expansion bus interface 114 are connected to PCI local bus 106 by direct component connection. In contrast, audio adapter 116, graphics adapter 318, and audio/video adapter 119 are connected to PCI local bus 106 by add-in boards inserted into expansion slots. Expansion bus interface 314 provides a connection for a keyboard and mouse adapter 120, modem 122, and additional memory 124. Small computer system interface (SCSI) host bus adapter 112 provides a connection for hard disk drive 126, tape drive 128, and CD-ROM drive 130.

An operating system runs on processor 102 and is used to coordinate and provide control of various components within data processing system 100 in FIG. 1. The operating system may be a commercially available operating system, such as a Windows operating system. Instructions for the operating system and applications or programs are located on storage devices, such as hard disk drive 126, and may be loaded into main memory 104 for execution by processor 102.

Those of ordinary skill in the art will appreciate that the hardware in FIG. 1 may vary depending on the implementation. The depicted example is not meant to imply architectural limitations with respect to the disclosed embodiments. For example, data processing system 100 also may be a notebook computer or hand held computer or another suitable data processing system.

Figure 2:
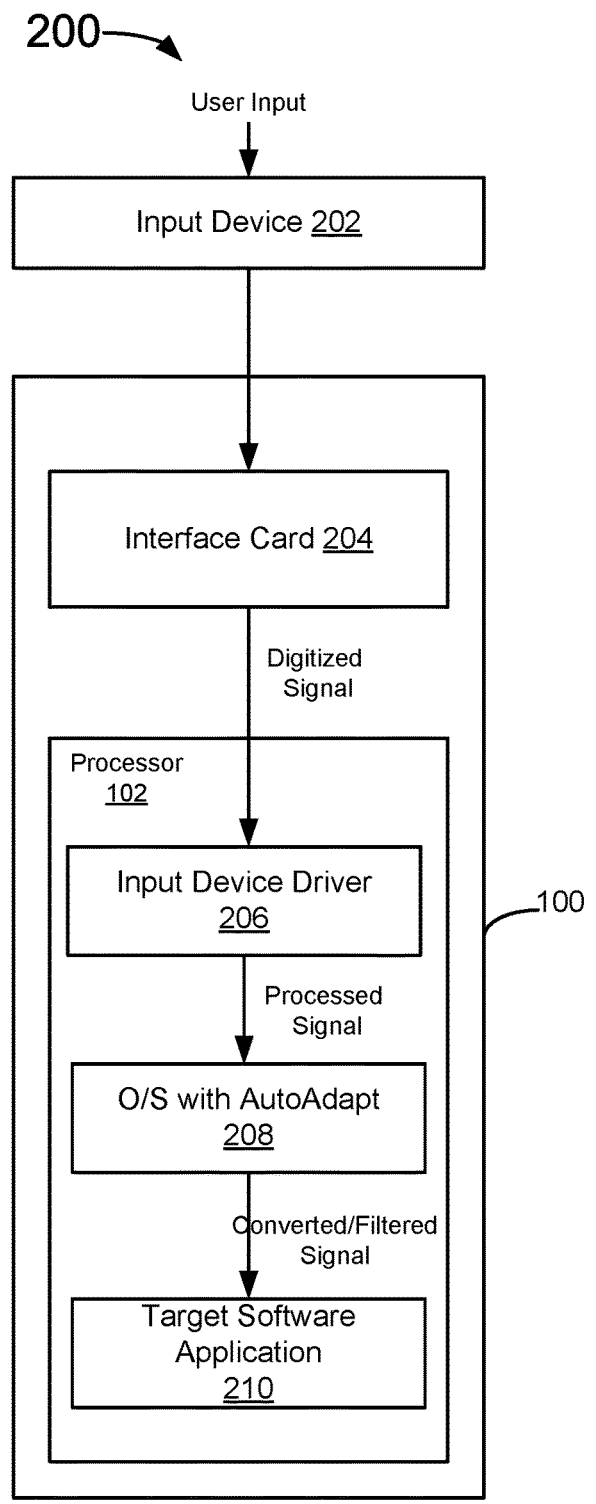
FIG. 2 is a diagrammatic representation of a system configuration that facilitates application auto-adaptation mechanisms implemented in accordance with an embodiment.

FIG. 2 is a diagrammatic representation of a system configuration that facilitates application auto-adaptation mechanisms implemented in accordance with an embodiment. A user supplies input to an input device 202, e.g., a keyboard, mouse, mouth stick, sip/puff system, or another suitable input device. In the illustrative example, the input is directed to a non-accessibility enhanced target software application 210. The input is then supplied to a system input port, an interface card 204, as an electrical signal. The interface card may comprise, for example, a PCI interface card, a USB interface card, or another suitable technology. The signal is digitized and sent to a device driver 206 of the input device 202. A processed signal produced by the driver is transmitted to the system operating system (O/S) 208 that features AutoAdapt technologies implemented in accordance with an embodiment. The AutoAdapt component integrated or interfaced with the operating system may then convert and/or filter the signal by mapping the signal level to known discrete or continuous software inputs using mechanisms described more fully hereinbelow. For example, a signal level may be mapped to a discrete input (e.g., a medium activation of a muscle may lead to a medium signal level at the computer which the AutoAdapt mechanism converts into a right mouse button click). The converted signal is then passed to the target software application 210, which will read the signal as a regular device input.

Figure 3:
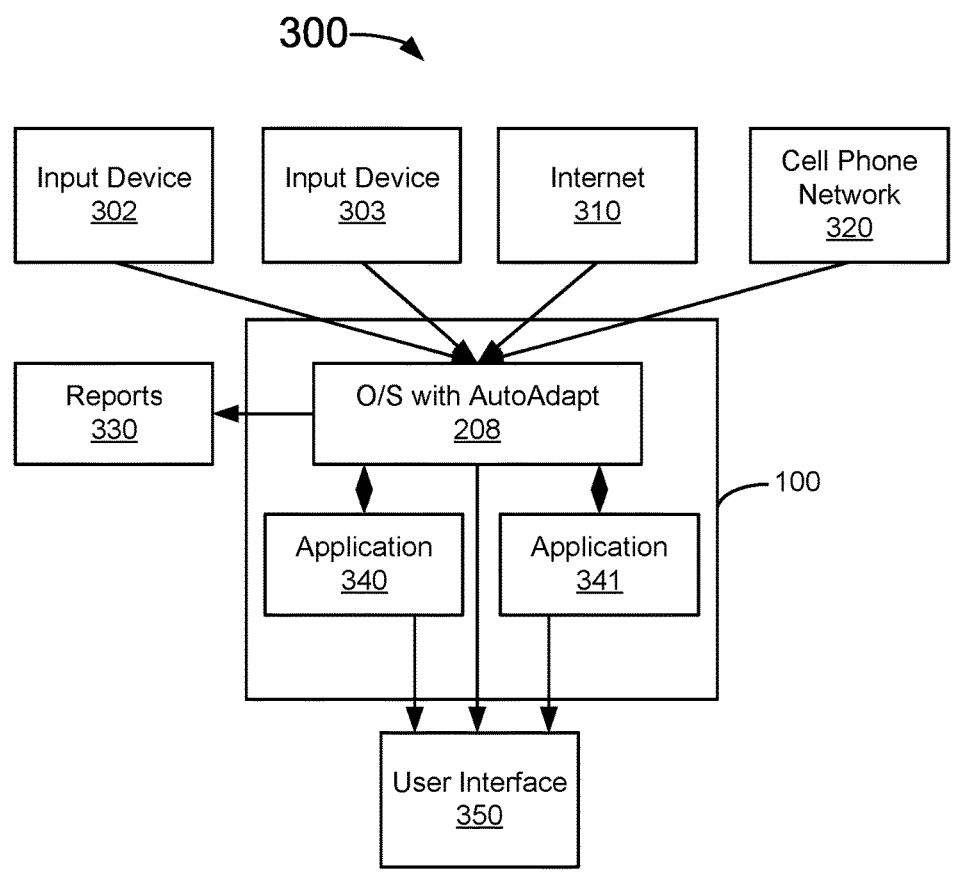
FIG. 3 is a diagrammatic representation of an exemplary system configuration in which a data processing system features the auto-adaptation mechanisms in accordance with disclosed embodiments.

FIG. 3 is a diagrammatic representation 300 of an exemplary system configuration in which a data processing system features the auto-adaptation mechanisms in accordance with disclosed embodiments.

In the depicted system configuration, a user may supply input at one or more input devices 302-303, such as a mouse, keyboard, or other device, of the data processing system 100. The user supplied input is provided by a user interacting with a target application, such as an application 340-341. The input is then supplied to the system operating system 208 that features or interfaces with auto-adaptation mechanisms implemented in accordance with an embodiment. Further, one or more networks, such as the Internet 310 and/or a cell phone network 320, may be communicatively interfaced with the operating system 208. The operating system 208 processes input and is communicatively coupled with the applications 340-341. Further, the operating system is communicatively coupled with a user interface, e.g., provided on a monitor, by which the user interacts with the system. The operating system may generate reports 330 of the auto-adaptation processing.

The AutoAdapt module integrated or otherwise interfaced with the operating system may include a configuration screen that may be displayed to the user on the initial system startup. An able-bodied user who has no use for the assistive functionality may disable the AutoAdapt module unless there was certain functionality that was helpful to the able-bodied user.

The AutoAdapt module may initially be configured to provide the most basic level of functionality, e.g., configured with a single input device. The user is then tested by the AutoAdapt module for the user's capabilities by way of questions submitted to the user and/or tasks to evaluate the user's performance. The complexity may then increase as the system identifies the individual's capabilities.

In an embodiment, a number of considerations may be made when performing adaptation processing. One such consideration is determining what questions may facilitate the system to an accurate understanding of the capabilities of the user. As such, the questions submitted to the user may be tailored and adapted based on answers to previous questions.

A second consideration is how the user is able to physically answer the questions, e.g., by a single switch or button, a keyboard, etc. In this manner, a format is determined for the questions to be submitted to the user and how the questions should be presented. For example, a user with a single switch for use as an input device to the system cannot be asked a multiple choice question without some capability on the system's part to toggle between the choices. On the other hand, if a person can operate a full keyboard, the same multiple choice question may be presented to the user without employing an automatic answer toggling system. The above issues are processed during an assessment stage of the customization process.

One customization step in AutoAdapt is therefore to evaluate the nature of an individual's input capabilities. That is, the system may seek to determine what inputs the user may reliably send into the computer or other data processing system. With this information, the AutoAdapt mechanisms may focus on ascertaining the quality of the user inputs, e.g., determining if the user can control a mouse, how precisely can the user position the mouse, etc.

As noted above, the AutoAdapt module may initially assume that the user has access to only one input device, such as a switch. Further, the AutoAdapt module may not be informed if the user has any other disabilities. Accordingly, early questions submitted to the user may be presented onscreen and spoken aloud. Such a question presentation to the user may continue until the user directs the AutoAdapt module for another question presentation. To this end, after a question is presented to the user, the question may also be visually displayed and audibly presented to the user. In accordance with an embodiment, a question presented to the user may have a Boolean response, i.e., a True ("Yes") or False ("No") answer. A timer may be invoked that visibly and/or audibly counts down from any number, such as 5. When it reaches 0, the process is repeated with a negative, e.g., "No.", response to the answer. If the question is not a yes/no question, the buttons or other interactive features may change accordingly, but the same automatic toggling procedure will be invoked. In an embodiment, a currently highlighted button at the time of the user click is the selected choice.

Notably, because of the wide variety of assistive hardware devices and the variability in user abilities, it may be impractical to provide a full script of a complete adaptive process. Therefore, the particular procedures described below are only provided as an example to facilitate an understanding of the disclosed embodiments.

Figure 4:
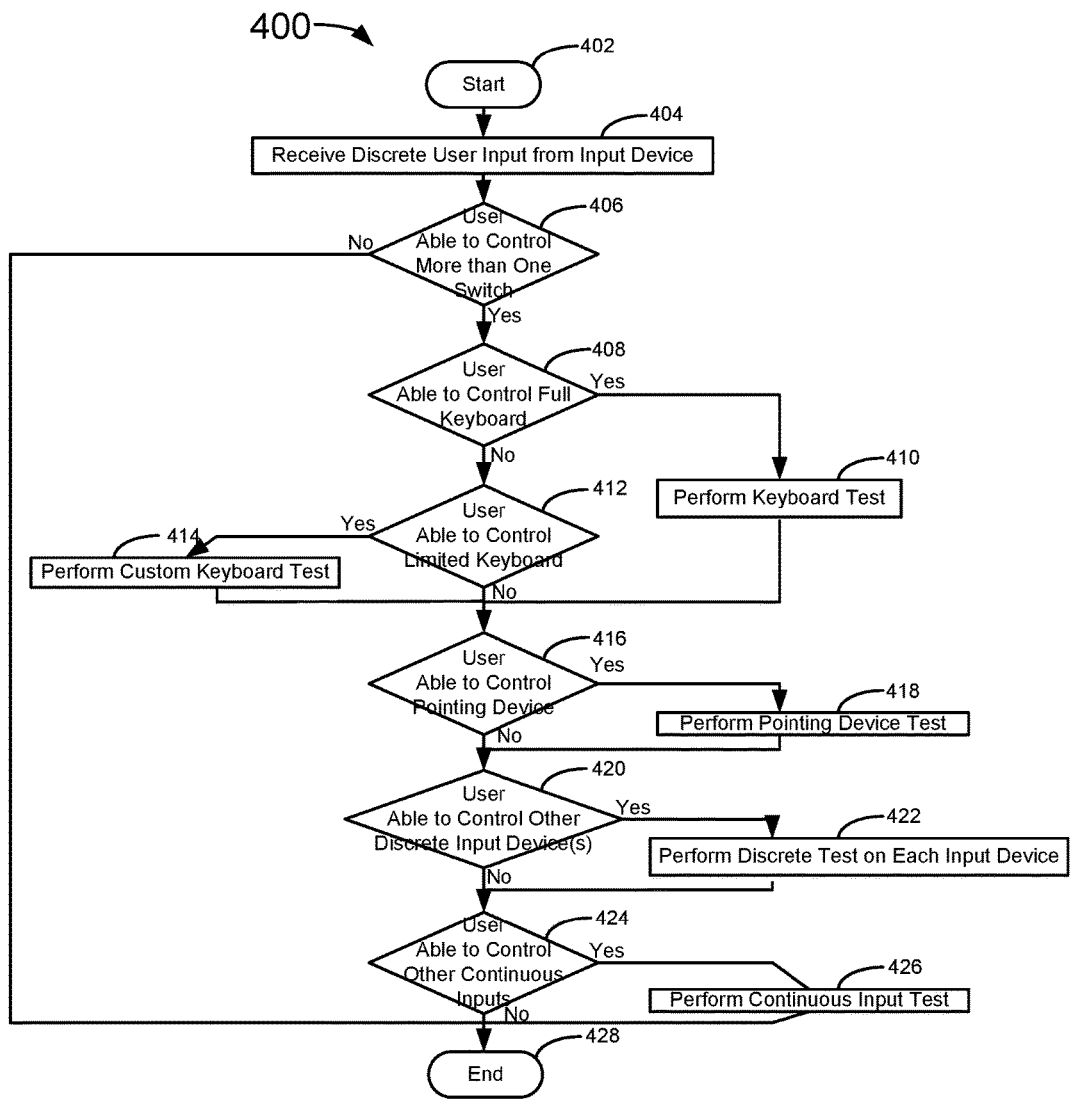
FIG. 4 is a flowchart of an exemplary auto-adaptation routine implemented in accordance with an embodiment.

FIG. 4 is a flowchart of an exemplary auto-adaptation routine implemented in accordance with an embodiment. The processing steps of FIG. 4 may be implemented as computer-executable instructions tangibly embodied on a computer-readable medium executable by a processing system, such as the data processing system 100 depicted in FIG. 1.

The auto-adaptation routine is invoked (step 402), and a discrete user input is received by the auto-adaptation module (step 404). The discrete input comprises an input that has one or more distinct states, such as "on" and "off". For example, the discrete input may comprise input provided to a mouse button or an external on/off switch. Keyboards may also be utilized for providing discrete input, although they may be addressed in a separate stage of the testing. Inputs provided during a user testing stage may comprise signals that are provided from, for example, recording electrodes placed on muscles of a user, devices that indicate the position of a user's head, or the like.

The auto-adaptation module then evaluates the input to determine if the user is able to control more than one switch (step 406). If the user is determined to not be able to control more than one switch, the auto-adaptation routine cycle may then end (step 428). If the user is able to control more than one switch, an evaluation may then be made to determine if the user is able to control a fully operational keyboard (step 408). If the user is able to control a fully operational keyboard, the processing module may then invoke and perform a keyboard test (step 410). The processing module may then perform an evaluation of whether the user is able to control a pointing device (step 416).

Returning again to step 408, if the user is not able to control a fully operation keyboard, the processing module may then evaluate whether the user is able to control a limited keyboard (step 412). If so, the auto-adapt module may then perform a custom keyboard test (step 414), and thereafter evaluate whether the user is able to control a pointing device according to step 416.

Returning again to step 412, in the event the user is not able to control a limited keyboard, the processing routine may then proceed to evaluate whether the user is able to control a pointing device according to step 416. If the user is able to control a pointing device, then the processing routine may then proceed to perform a pointing device test (step 418), and the processing routine may then proceed to evaluate whether the user is able to control other discrete input devices (step 420). If, at step 416, the optimizer determines that the user is not able to control a pointing device, the system may then proceed to determine whether the user is able to control other discrete input devices according to step 420. In the event that the user is able to control other discrete input devices, the system may then perform a discrete test on each identified device (step 422), and the system may then proceed to evaluate whether the user has control over other continuous inputs (step 424). In the event that it is determined that the user is not able to control other discrete continuous input devices, the processing routine cycle may then complete (step 428).

As an exemplary description of questions that may be presented to a user for purposes of evaluating the user's capabilities, the system may prompt the user with questions including: what is the optimum text size for the user (a list of choices may be shown); how large would the user desire the cursor to be (a list of choice may be shown for the user's selection); whether the user desires to continue hearing spoken instructions; whether the user desires to continue seeing the written instructions, and the like.

In accordance with embodiments, discrete input tests are utilized and are designed to assess the ability of the user to a single or multiple click input device, and/or a hold of an external on/off switch, such as a mouse button or an external switch. In this manner, the disclosed mechanisms provide for asking the user to click or otherwise select the device on cue and to hold the click as long as the onscreen prompt indicates. Examples could comprise a single click, double click, and click and hold for variable durations. In the case of multiple discrete inputs, the system may query the user to see if the user is able to activate multiple inputs simultaneously. If so, the user may be prompted to input in the same way as in the single key activation case. The two keys together may provide another potential state. For example, if the user is able to select button 1, button 2, and button 1 and 2 simultaneously, the two buttons may provide three distinct discrete inputs. These discrete input tests may provide valuable information to the system, such as how quickly a user can activate the switch and the user's ability to hold and/or release the switch on cue.

Figure 5:
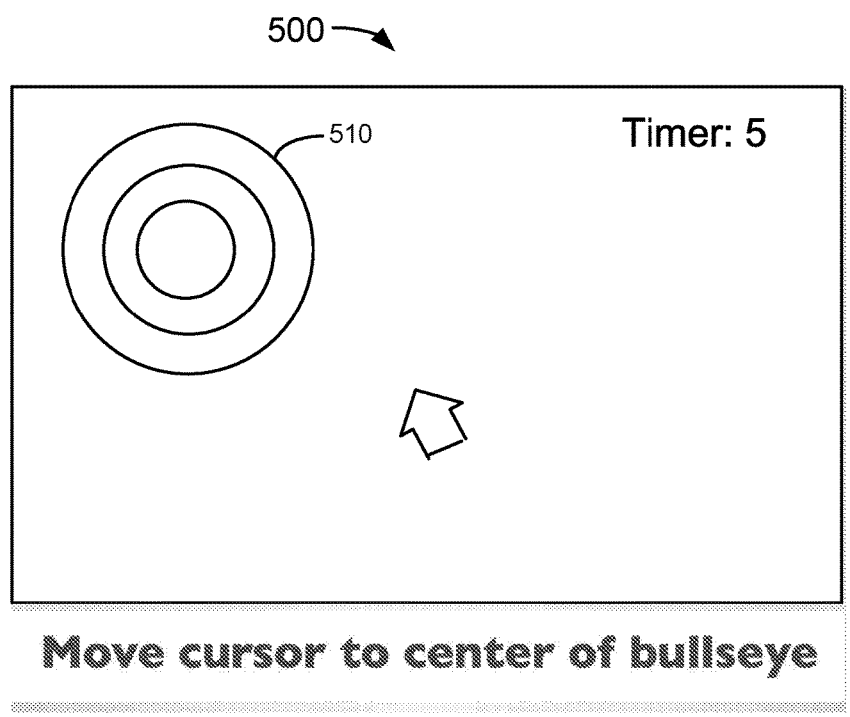
FIG. 5 depicts a diagrammatic representation of a pointing test implemented in accordance with disclosed embodiments.

In an embodiment, a "pointing test" may be invoked with verbal and written instructions to follow, for example, a large bulls-eye on a display device. FIG. 5 depicts a diagrammatic representation 500 of a pointing test implemented in accordance with disclosed embodiments. A "bulls-eye" graphical representation 510, or other target, may initially move to a point on the screen and remain at the selected placement. Once the user stops moving the cursor for a predefined period of time, e.g., five seconds, or after another predefined period of time, e.g., ten seconds, have elapsed, the software may then move the bulls-eye graphical representation 510 to another position. The described mechanism may be repeated several times. Based on the user's ability to maintain the cursor on the bull's eye graphical representation 410, the software is able to evaluate how precisely and consistently the user is able to control a pointing device.

In an embodiment, the "simulated pointing test" depicted and described with reference to FIG. 5 comprises a cursor system in which the software systematically breaks the screen into subregions, and thereafter allows the user to select a subregion by clicking an onscreen button, e.g., through a mouse click or external switch activation, when the region of interest is highlighted. Once the selection is performed, subregions within the selected regions may be highlighted one at a time. This may be performed until the system has honed in on the requested position. In accordance with this mechanism, the system may analyze how rapidly the user is able to choose a particular point and will update its speed accordingly.

Keyboard proficiency may be assessed in a manner similar to the pointing test described above, although instead of following a particular point of interest (e.g., a bulls-eye) with a pointer, in this implementation the user may be directed to copy characters that are displayed to the user. In this implementation, the user may be provisioned a test that may incorporate a "click and hold" testing mechanism described above with regard to the "discrete input test" in order to determine, among other things, if the user has a problem with inadvertently hitting a particular key multiple times or, for example, holding a particular key down too long, both of which may cause multiple characters to be typed. It may also add a test of holding multiple keys at once for cases in which a modifier is needed, such as the Shift-Lock key. These tests may indicate if the user needs to have access to such keyboard modifications as "Sticky Keys" (e.g., hitting shift causes it to "stick," combining it with the next typed keys as though they were pressed simultaneously), "Slow Keys" (e.g., only accepting a key input if the key is held for a given length of time), or "Bounce Keys" (e.g., ignoring quick successive entry of the same key). As in the discrete input case, multiple simultaneous key presses may be considered additional inputs for those cases in which the keyboard has a limited number of keys.

Virtual onscreen keyboard proficiency may be tested in a manner similar to the keyboard proficiency test above in accordance with an embodiment, although it may additionally incorporate features of the pointing test. If the user has access to a pointer, then the test may be similar to the "pointing test" because the user may be using a pointer to type in the keys on the screen. Alternatively, if the user uses the onscreen keyboard's toggling system with an external switch, e.g., because the user doesn't have use of a pointing device or, for example, because the user chooses to use the toggling system, then the testing may be implemented more similar to the "simulated pointing test." In this manner, the user may be responding via a click to toggling states on the computer.

"Continuous input tests" may determine the user's ability to handle continuous input signals. With regard to continuous user inputs, continuous signals, as opposed to discrete signals such as button clicks or key presses, have a continuously variable input level. An example of a continuous signal comprises a recording of muscle activity from an electrode placed on the skin or a graph of varying patterns from an EEG. Typically, these signals do not map directly into the computer other than in those cases in which such signals are recorded for use in academic pursuits. The AutoAdapt mechanisms disclosed herein may advantageously provide an interface for continuous signals.

As with any external signal, hardware is needed in order to convert a signal into a form that a computer may utilize. For example, a mouse is needed to convert a hand movement into the electrical signal that indicates to the computer where the cursor should be located. An appropriate input device for continuous signals comprises a data acquisition card (DAQ) that may be interfaced with an available port, e.g., a PCI port, on the computer. In accordance with the disclosed mechanisms, it is assumed that hardware is present such that any external signal is converted into a form that the computer may process.

In accordance with this embodiment, the computer may receive one or more variable continuous signals from a user. The most important consideration for the disclosed AutoAdapt mechanism is the ability to determine how many stable input signals may be derived out of these signals. For example, if an individual has one continuous channel, e.g., one signal from a single recording electrode, then the user may be able to create three different inputs: a high activation, low activation, and off. On the other hand, the AutoAdapt mechanism may determine that the user has no ability to consistently control a given channel with sufficient reliability in order to use that signal as an input source. This system logic may also hold true for each channel in multiple channel environments.

As an example, assume that a user has a recording electrode on the muscles on each side of the user's neck, and that these electrodes lead to two channels of information interfaced and supplied into a computer. If the user can flex each side of his neck at a low and high level, then each electrode has three possible states, e.g., off, low, high. If each side of the neck can be controlled by the individual independently, then these 2 continuous signals lead to 9 possible input states, e.g., off/off, off/low, off/high, low/off, low/low, low/high, high/off, high/low, high/high. If, however, the AutoAdapt module determines that the two signals are always correlated, that is that when one goes high then the other proceeds high responsive thereto, then the system is reduced to only 3 states, and one of the channels is redundant.

Alternatively, a benefit of the disclosed AutoAdapt mechanism is that it can adapt to a user as his condition changes. Concentrated practice on sending graded continuous inputs into a computer may possibly increase the user's proficiency with the available control signals. In the above case, this may lead to the two signals once again becoming independent. Or, again referring to the above example, a user may become so proficient at controlling the user's neck muscles that the user may maintain 4 distinct activation levels per channel, (e.g., off, low, medium, and high), thereby leading to an increase to possibly 16 distinctive input states based on the two independent continuous data channels.

The disclosed AutoAdapt mechanism analyzes a user's ability to control a continuous signal through a quizzing mechanism that involves user biofeedback. During the continuous signal analysis phase of the configuration, the system may show the user a real-time display of all available continuous channels. The user may be able to recognize changes in displayed signal levels in real-time. Using the above example, a user flexing the left side of his neck may visually identify a trace that indicates the left signal level increase accordingly. This may advantageously facilitate the user learning the required regime to control such signals.

In accordance with an embodiment, after a user-determined period of freeform experimentation and practice by the user, the AutoAdapt module may seek to assess the individual's ability to control the input signals, both as a group and individually. To this end, the system may request the user to activate each signal in turn to a "high" state. After this, the process may be repeated, but the system may then request that all other signals be left at their default (presumably low) state. The individual's performance will provide the AutoAdapt module with information regarding how independent the given signals are. Once the system has tested the individuals on each channel, it may repeat the process but request a "low" state. Once the system completes this analysis, it will return to those signals that were shown to be controllable by the user. Each of these will be analyzed in turn. The system may then ask the user to activate each of the signals in, for example, one of five (or more, if needed) states. If the system is able to differentiate between a plurality of distinct, e.g., five, distinct states, then that one channel provides for five separate inputs to the system. Otherwise, the system may determine how many states it can create out of the inputs. For example, it may determine that the user really only has a low and a high activation level for each channel.

Figure 6:
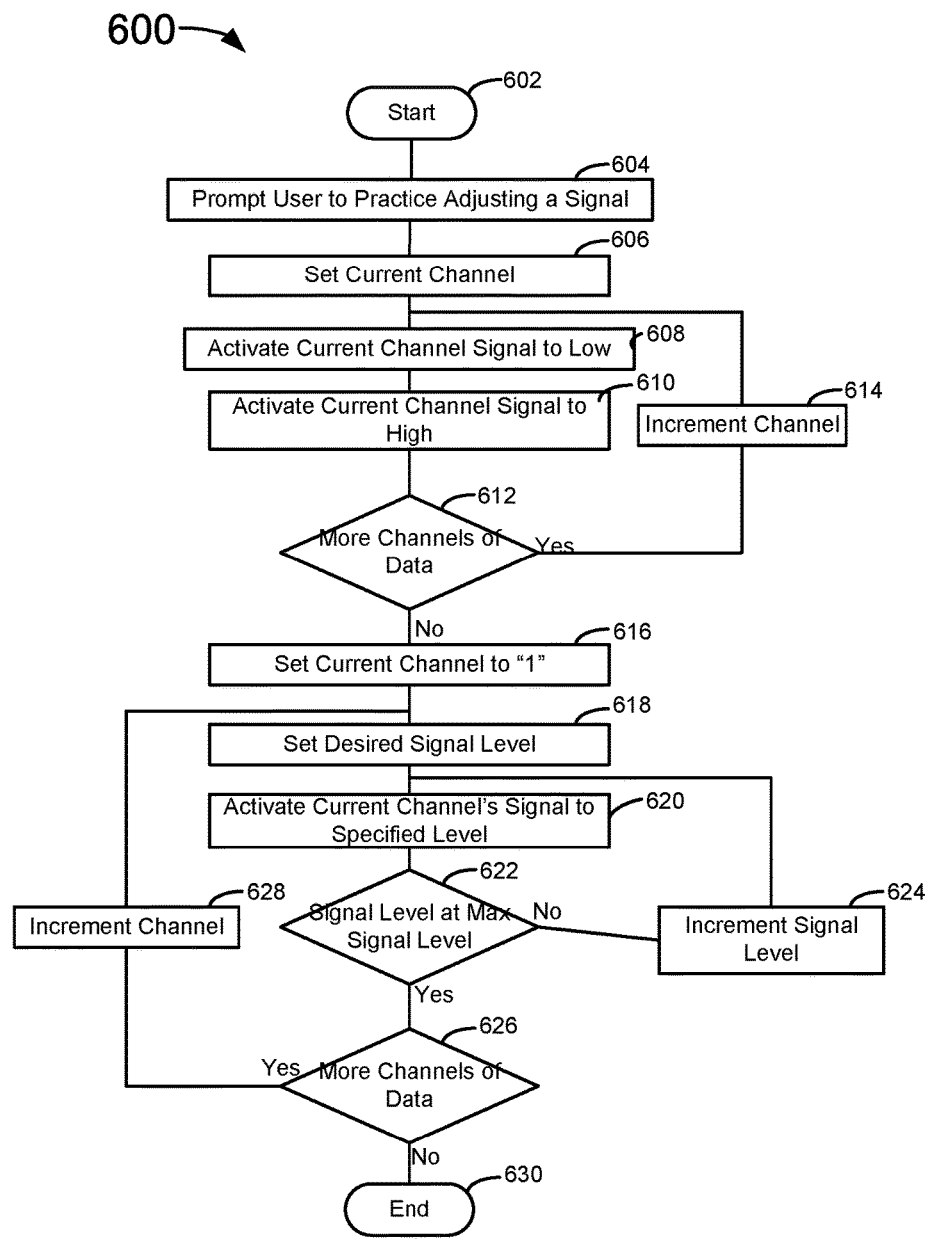
FIG. 6 depicts a flowchart of an auto-adaptation routine for assessing a user's ability to control an input signal in accordance with an embodiment.

FIG. 6 depicts a flowchart 600 of an auto-adaptation routine for assessing a user's ability to control an input signal in accordance with an embodiment. The processing steps of FIG. 6 may be implemented as computer-executable instructions tangibly embodied on a computer-readable medium executable by a processing system, such as the data processing system 100 depicted in FIG. 1.

The auto-adaptation routine is invoked (step 602), and the user is prompted to practice adjusting a signal (step 604). The current channel is then set, e.g., to "1", (step 606), and the current channel signal is activated to a low value (step 608). The current channel signal may then be activated to a high value (step 610). An evaluation is then made to determine if more channels of data are available (step 612). If so, the channel is incremented (step 614), and the auto-adaptation routine may then return to activate the channel signal to low according to step 608.

When no additional channels of data are available, the auto-adaptation routine may then set the current channel to "1" (step 616) and set the desired signal level (step 618), e.g., to one of the available states. The current channel's signal is then set to the specified level (step 620). An evaluation may be made to determine if the signal level is set to the maximum signal level (step 622). If not, the signal level may be incremented (step 624), and the auto-adaptation routine may then set the current channel's signal to the specified level according to step 620.

When the signal level is evaluated as being set to the maximum level, the auto-adaptation routine may then proceed to evaluate whether more channels of data are available (step 626). If so, the auto-adaptation routine may then proceed to increment the channel (step 628) and set the desired signal level according to step 618. When no additional channels of data are available, the auto-adaptation routine cycle may then end (step 630).

In some cases, the user may have enough control of two independent continuous channels that the user can control an input device, e.g., a mouse, using these signals. One example would be for one signal to indicate horizontal movement while the other indicates vertical movement.

A final phase provides for customization that facilitates adapting or mapping the user's capabilities determined during the assessment phase described above to the electronic system's input requirements.

Once the user's abilities are assessed, this information may be made available to other software applications running on the computer. If the AutoAdapt module is integrated with the operating system, then the operating system may be automatically provided with this information. Actively running applications may also be provided with this information in the same manner that applications already use to communicate with the operating system in order to determine system parameters, such as the current time. The calls that would provide the data may be implemented as part of the operating systems application programming interface (API).

The O/S may take direct action by modifying the O/S's interface based on the assessment. For example, if the assessment indicates that the user prefers a larger font, then all menus controlled by the O/S may be modified with the larger font.

This data may also be particularly important for accessible applications which can process non-standard inputs. These applications may be provided access to the user's capabilities such that they may adjust their applications accordingly. For example, if the assessments indicate that the user takes a long time to activate an input switch, the application may slow down the timing when toggling through choices. Another example would be if the assessments indicate that a user has access to a pointing device, such as a modified mouse or trackball, but the user has limited precision with the device, the software application may provide input buttons or controls in a larger format.

Another benefit of the AutoAdapt system is for those cases in which the application being used is not aware of a user's disability or does not contain assistive features. In this case, the inputs into the application must appear exactly like mouse and keyboard inputs, as in the typical use case. For these, the AutoAdapt module may perform as an accessibility layer, translating user inputs into usable software inputs. For example, if the user has learned to control a pointing device using four channels from a brain wave analyzer, the AutoAdapt module may convert these signals into a two dimensional movement and feed that into the software application as though it were from a physical external mouse. Because of these abilities, users are advantageously not limited to software that is compatible with assistive technology. Rather, such mechanisms make available a wide range of software applications to the user.

In addition to these user interface modifications, the adaption phase may involve creating macros to simplify multistep actions with a single input. The macros may be created with different levels of complexity. Based on the user's capabilities, the user input to the macro may vary (e.g., keypress or muscle activation), and the number of steps in the desired outcome may likewise vary based on the user's needs. For example, one simple macro might be activated when the user simultaneously hits the control key and the 'o' key, for example, causing a new browser window to be opened. That single "control-o" keypress replaced a multistep process in which the user would have had to use his mouse to launch the browser application. A more complicated macro could be when a user performs a given motion with the user's mouth stick, then the user's email client is launched and a new email is created with an email address pre-populated.

The most straightforward manner to create macros is to utilize a recording function. Essentially, the user may start a macro-recording mode of the AutoAdapt module, perform the desired procedures manually that the macro is to perform automatically when launched, then stop the recording. A second step is for the user to indicate to the AutoAdapt module what input to use to initiate the macro in the future. When the user later initiates the macro by entering the input, the steps recorded during the macro setup phase will be executed. In this manner, a user may create a macro that could perform any action available on the device.

For those cases in which a user's capabilities indicate that they can have options concerning how to interact with the system, e.g., they may either use a pointing device with an onscreen keyboard or use an external keyboard, the user may be asked questions about their preferences. For instance, the user may be asked how the user would like to control a pointer—with a scanning technique and external switch, with an external keyboard mapped to different regions of the screen, or with two independent continuous input signals. As another example, the user may be asked how the user would like to input text—using a microphone with speech recognition software or via an onscreen keyboard. As another example, the user may be asked, regarding an onscreen keyboard, would the user like to use a pointing device to type the keys or use a toggling system with an external switch. For applications that provide their own accessible onscreen keyboard, the user may be asked if the user would prefer to disable the AutoAdapt module's onscreen keyboard and use the one provided by the software application. In addition to the customization steps of assessment and adaptation described above, disclosed mechanisms provide two additional modes of operation: a training mode and a continuous assessment mode.

The training mode is an optional mode that facilitates assisting a user to increase proficiency with an input device. The training mode is interactive, and as such it may automatically adjust the difficulty level of the testing based on the user's previous performance. This operational mode facilitates increasing the user's speed and precision with an input device, such as a pointing device.

Because many computer games, for instance, require speed and precision with input devices, games may provide an exemplary mechanism to provide the user with training. The training mode is preferably configured to reduce or eliminate a user's frustration in an initial lack of proficiency. Therefore, as is the general case, the operational difficulty of the activities, e.g., games, of the training mode may automatically be adjusted based on the user's capabilities. This may be accomplished using the same procedure that is used for other applications, namely the assessment information may be provided to the game application. The application may then take advantage of this information to adjust the parameters of the game.

Well-designed games hold several advantages when integrating a new input system into an electronic device. In addition to the training benefits described above, gaming applications may also remove a significant barrier to success for the system. For example, the user may not perform training unless motivated. Enjoyable games may often provide sufficient motivation, and users may not realize that they are being trained. Another advantage of gaming applications is that, as part of the training, the system is actually gathering important assessment information about the user.

A continuous assessment mode may operationally default as a background mode. The AutoAdapt module may monitor the user's activities and attempt to ascertain the user's abilities as performed during day-to-day computer activities. For example, when the user moves the pointer to a button and clicks it, the AutoAdapt module may be able to analyze the pointer's trajectory. Several features of the trajectory may be extracted, such as its velocity profile, e.g., how smoothly did it accelerate and decelerate, and its position over time, e.g., did the mouse move in a single straight line to the target, or were there several shorter adjustments that could indicate a difficulty with positioning. These trajectory features may be compared to data from typical users to determine if the data provides other subtle clues about the user's proficiency. In addition, for a customized assessment, the user may use a known pointing device with which the user has a high proficiency in order to train the system. In effect, using this technique, the user thereby indicates that the user desires to operate the new pointing device in the same manner as the current pointing device.

Another example of a continuous assessment opportunity is on a computer that uses a pointer or virtual keyboard system that toggles through choices, waiting on a mouse click. On this system, the AutoAdapt module may be able to detect when a user misses their desired choice. For example, when an individual is typing by using a single switch and a virtual onscreen keyboard with software that toggles through rows of keys and then through the keys themselves, it operates by toggling through choices until a user clicks a selection, and then toggles through sub-choices in the same manner until the final selection is made. When the system detects that a given choice has to be presented multiple times before the user is able to provide a selection indicating that the user missed the opportunity to make the selection on the first display of the option, then the system may deduce that the user isn't being provided enough time to respond. The software toggling system may then be slowed accordingly.

On the other hand, some information gleaned from continuous assessment may be ambiguous because the system isn't aware of the user's intent. For example, because a user doesn't precisely click the center of a button doesn't necessarily indicate that the user could not do so. Rather, it may indicate that the user was efficient and clicked the corner of the button closest to the pointer's starting position. However, if the system detects the user moving the pointer past a button, stopping, then immediately moving the pointer to the button, then the assumption is that the first movement was a missed attempt by the user to point to the button. If the system identifies such a situation repeatedly, then the AutoAdapt module may deduce that the user is having difficulty with the pointing device.

Note that the initial assessment mode testing is more rigorous than the continuous assessment mode because the former has more control over the variables. Namely, in the assessment mode tests, the system directly measures the features it is attempting to analyze, such as the user's speed with moving the pointer. On the other hand, the continuous assessment mode depends on the current activities for the testing. For example, if the user is simply clicking buttons as the user progresses through an online photo album, the system may test how accurately the user selects a button. However, it doesn't necessarily identify if the user was attempting to select the center of the button, or if the user was moving the pointer as fast as the user possibly could. Because of this, the continuous assessment mode is preferably conservative in its estimation of user skills.

Figure 7:
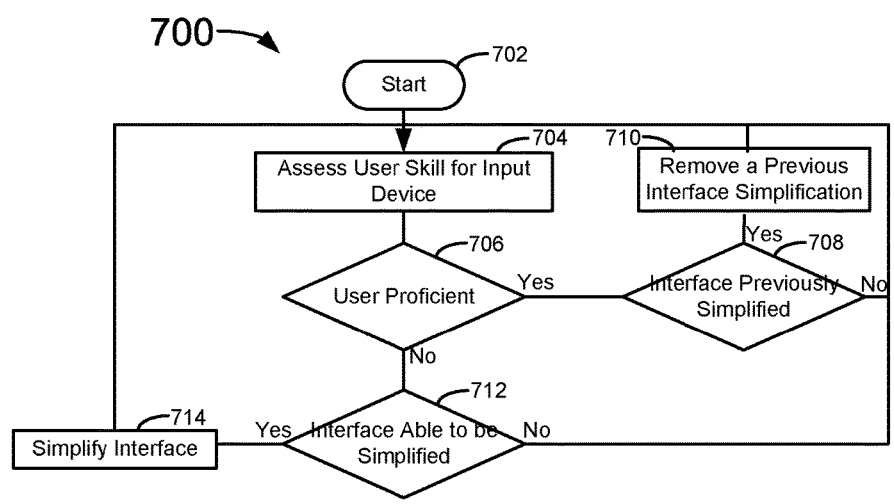
FIG. 7 depicts a flowchart of an auto-adaptation continuous user assessment routine for assessing a user's ability in accordance with an embodiment.

FIG. 7 depicts a flowchart 700 of an auto-adaptation continuous user assessment routine for assessing a user's ability in accordance with an embodiment. The processing steps of FIG. 7 may be implemented as computer-executable instructions tangibly embodied on a computer-readable medium executable by a processing system, such as the data processing system 100 depicted in FIG. 1.

The continuous user assessment routine is invoked (step 702), and an evaluation of a user skill with regard to an input device is performed (step 704). An evaluation is then made to determine if the user is proficient with the input device (step 706). If the user is assessed as proficient, an evaluation may then be made to determine if the user interface has previously been simplified (step 708). If so, the previous interface simplification may then be removed (step 710), and the user assessment routine may then return to assess the user skill for the input device according to step 704. If the interface was not previously simplified, the user assessment routine may then return to assess the skill for the input device according to step 704.

Returning again to step 706, if the user is evaluated as not sufficiently proficient with the input device, an evaluation may be made to determine if the interface is able to be simplified to facilitate proficient input by the user (step 712). If so, the interface may be simplified (step 714), and the user assessment routine may then return to assess the user skill for the input device according to step 704. If the user interface may not be simplified, the user assessment routine may then return to assess the user skill for the input device according to step 704.

The described examples are exemplary of the ongoing assessment that the system may perform. In addition, the user may request an updated initial assessment in which case the user may rerun the initial setup wizard.

Another benefit of AutoAdapt mechanism is that it may store the user's ongoing assessment scores so that user progress may be tracked by caregivers. This would provide valuable data concerning the evolution of the individual's abilities. For example, in the case of a person with a physical disability, the user's ability to use a computer pointing device, or other input device, may likely vary with time. The user's motor ability may be influenced by several factors, including the nature of the user's condition, e.g., if it's degenerative, the amount of practice the user has performed using the device, outside occupational therapy, and the like.

As another example, a physical therapist who recently introduced a new exercise regimen may want to review the AutoAdapt data to evaluate if there was any change in the user's abilities that coincided with onset of the new therapy. The AutoAdapt module is uniquely positioned to provide this data because it is integrated into a high performance device, such as a computer, capable of storing vast amounts of data, it constantly logs user proficiency as part of its ongoing operation, it doesn't require a cumbersome testing procedure for the user because it runs in the background at all times, and it is likely deployed on a device that is used frequently.

As noted hereinabove, this data is also directly used by AutoAdapt module. It monitors for both improvements and reductions in efficiency by the user. It may fine-tune the interface as the user's needs progress, such as reducing time delays previously added to accommodate slow user response when it determines that the user doesn't need the extra time, or it may offer entirely new options once the user's abilities pass certain milestones. An example of the latter is in the event the data indicated that the user's vision improved such that an application's text size was returned to normal, the AutoAdapt module may offer the option of removing any additional verbal prompts that were initially added due to the user's poor vision. Another example would be if an able-bodied user had gained enough proficiency with a new pointing device such that a smoothing filter previously applied to the pointer trajectory may be disabled.

As described, mechanisms of the disclosed embodiments facilitate software configuration of assistive computer devices by automatically assessing a user's capabilities through questions and tasks. The analysis results of the user's capabilities then become available to assistive computer software applications which may subsequently update their interfaces accordingly. Further, a "mapping" from an external input device into a target software application may be facilitated for software applications that do not include assistive technology features. In this manner, a previously inaccessible application may be made accessible to a user. Further, disclosed mechanisms improve the ongoing user experience by continually evaluating the user's capabilities and updating the stored assessment of the user's capabilities.

The flowcharts of FIGS. 4 and 6-7 depict process serialization to facilitate an understanding of disclosed embodiments and are not necessarily indicative of the serialization of the operations being performed. In various embodiments, the processing steps described in FIGS. 4 and 6-7 may be performed in varying order, and one or more depicted steps may be performed in parallel with other steps. Additionally, execution of some processing steps of FIGS. 4 and 6-7 may be excluded without departing from embodiments disclosed herein.

The illustrative block diagrams depict process steps or blocks that may represent modules, segments, or portions of code that include one or more executable instructions for implementing specific logical functions or steps in the process. Although the particular examples illustrate specific process steps or procedures, many alternative implementations are possible and may be made by simple design choice. Some process steps may be executed in different order from the specific description herein based on, for example, considerations of function, purpose, conformance to standard, legacy structure, user interface design, and the like.

Aspects of the present invention may be implemented in software, hardware, firmware, or a combination thereof. The various elements of the system, either individually or in combination, may be implemented as a computer program product tangibly embodied in a machine-readable storage device for execution by a processing unit. Various steps of embodiments of the invention may be performed by a computer processor executing a program tangibly embodied on a computer-readable medium to perform functions by operating on input and generating output. The computer-readable medium may be, for example, a memory, a transportable medium such as a compact disk, a floppy disk, or a diskette, such that a computer program embodying the aspects of the present invention can be loaded onto a computer. The computer program is not limited to any particular embodiment, and may, for example, be implemented in an operating system, application program, foreground or background process, driver, network stack, or any combination thereof, executing on a single processor or multiple processors. Additionally, various steps of embodiments of the invention may provide one or more data structures generated, produced, received, or otherwise implemented on a computer-readable medium, such as a memory.

Although embodiments of the present invention have been illustrated in the accompanied drawings and described in the foregoing description, it will be understood that the invention is not limited to the embodiments disclosed, but is capable of numerous rearrangements, modifications, and substitutions without departing from the spirit of the invention as set forth and defined by the following claims. For example, the capabilities of the invention can be performed fully and/or partially by one or more of the blocks, modules, processors or memories. Also, these capabilities may be performed in the current manner or in a distributed manner and on, or via, any device able to provide and/or receive information. Further, although depicted in a particular manner, various modules or blocks may be repositioned without departing from the scope of the current invention. Still further, although depicted in a particular manner, a greater or lesser number of modules and connections can be utilized with the present invention in order to accomplish the present invention, to provide additional known features to the present invention, and/or to make the present invention more efficient. Also, the information sent between various modules can be sent between the modules via at least one of a data network, the Internet, an Internet Protocol network, a wireless source, and a wired source and via plurality of protocols.

What is claimed is:

1. A method, comprising:
performing a proficiency test, by a data processing system, for an input device;
using the results of the proficiency test performed for the input device by the data processing system for modifying, by the data processing system, an operational characteristic of an interface of the data processing system; and
evaluating a user proficiency of the input device by a background assessment of the user's activities with the input device;
wherein the background assessment of the user's activities with the input device comprises:
receiving at least one signal from the input device for non-accessibility enhanced target software that is unable to perform the background assessment;
determining, from the at least one signal, by an adaptation module, the proficiency of the user with the input device and that an adjustment of the modification of the operational characteristic of the interface is required;
wherein the adjustment of the modification of the operational characteristic of the interface comprises:
adjusting at least one signal;
providing the adjusted at least one signal to the non-accessibility enhanced target software; and
wherein the modification of the operational characteristic of the interface is adjusted based on the background assessment.

2. The method of claim 1, wherein the proficiency test evaluates a quality of a user input supplied to the input device.

3. The method of claim 1, further comprising receiving, by the data processing system, an input signal from an input device channel, wherein the input signal comprises a variable level input signal.

4. The method of claim 3, further comprising determining, by the data processing system, a number of stable input signal levels that are derived from the variable level input signal.

5. The method of claim 1, further comprising:
determining that the user is proficiently skilled at utilizing the input device;
determining that a system user interface was previously simplified for the user; and
returning the user interface to an operational state utilized prior to simplification of the interface.

6. The method of claim 1, further comprising determining that the user is non-proficiently skilled at utilizing the input device.

7. The method of claim 6, further comprising simplifying a user interface of the data processing system responsive to determining the user is non-proficiently skilled at utilizing the input device.

8. A non-transitory computer-readable medium having computer-executable instructions for execution by a processing system that, when executed, cause the processing system to:
perform a proficiency test, by a data processing system, for an input device, wherein the proficiency test evaluates a quality of user input supplied to the input device;
modify an operational characteristic of a system user interface to modify how the data processing system responds to input from the input device based on results of the proficiency test performed for the input device; and
evaluate a user proficiency of the input device by a background assessment of the user's activities with the input device;
wherein, for the background assessment of the user's activities with the input device, the processing system is caused to:
receive at least one signal from the input device for non-accessibility enhanced target software that is unable to perform the background assessment;
determine, from the at least one signal, by an adaptation module, the proficiency of the user with the input device and that an adjustment of the modification of the operational characteristic of the interface is required; and
wherein, to adjust the modification of the operational characteristic of the interface, the processing system is caused to:
adjust the at least one signal;
provide the adjusted at least one signal to the non-accessibility enhanced target software; and
wherein the modification of the operational characteristic of the interface is adjusted based on the background assessment.

9. The non-transitory computer-readable medium of claim 8, further comprising instructions that, when executed, cause the processing system to receive, by the data processing system, an input signal from an input device channel, wherein the input signal comprises a variable level input signal.

10. The non-transitory computer-readable medium of claim 9, further comprising instructions that, when executed, cause the processing system to determine a number of stable input signal levels that are derived from the variable level input signal.

11. The non-transitory computer-readable medium of claim 8, further comprising instructions that, when executed, cause the processing system to:
determine that the user is proficiently skilled at utilizing the input device;
determine that the system user interface was previously simplified for the user; and
return the user interface to an operational state utilized prior to simplification of the interface.

12. The non-transitory computer-readable medium of claim 8, further comprising instructions that, when executed, cause the processing system to determine that the user is non-proficiently skilled at utilizing the input device.

13. The non-transitory computer-readable medium of claim 12, further comprising instructions that, when executed, cause the processing system to simplify the system user interface of the data processing system responsive to determining the user is non-proficiently skilled at utilizing the input device.

14. A system comprising:
a processing module;
a memory device including an adaptive software module; and
an input device, wherein the processing module performs a proficiency test for the input device, wherein the proficiency test evaluates a quality of user input supplied to the input device;

wherein the processing module evaluates a user proficiency of the input device by a background assessment of the user's activities with the input device; and wherein, for the background assessment of the user's activities with the input device, the processing module is configured to:

receive at least one signal from the input device for non-accessibility enhanced target software that is unable to perform the background assessment;

determine, from the at least one signal, by an adaptation module, the proficiency of the user with the input device and that an adjustment of modification of the operational characteristic of an interface is required; and wherein to adjust the modification of the operational characteristic of the interface, the processing module is configured to:

adjust the at least one signal;

provide the adjusted at least one signal to the non-accessibility enhanced target software; and wherein the modification of the operational characteristic of the interface is adjusted based on the background assessment.

15. The system of claim 14, wherein the processing module receives an input signal from an input device channel, wherein the input signal comprises a variable level input signal.

16. The system of claim 15, wherein the processing module determines a number of stable input signal levels that are derived from the variable level input signal.

17. The system of claim 14, wherein the processing module determines that the user is proficiently skilled at utilization of the input device, determines that a system user interface was previously simplified for the user, and returns the user interface to an operational state utilized prior to simplification of the interface.

* * * * *